(12) United States Patent
Bagherinia et al.

(10) Patent No.: US 9,101,294 B2
(45) Date of Patent: Aug. 11, 2015

(54) SYSTEMS AND METHODS FOR ENHANCED ACCURACY IN OCT IMAGING OF THE CORNEA

(71) Applicant: Carl Zeiss Meditec, Inc., Dublin, CA (US)

(72) Inventors: Homayoun Bagherinia, Oakland, CA (US); Utkarsh Sharma, San Ramon, CA (US)

(73) Assignee: Carl Zeiss Meditec, Inc., Dublin, CA (US)

( * ) Notice: Subject to any disclaimer, the term of this patent is extended or adjusted under 35 U.S.C. 154(b) by 91 days.

(21) Appl. No.: 13/744,102

(22) Filed: Jan. 17, 2013

(65) Prior Publication Data
US 2013/0188140 A1 Jul. 25, 2013

Related U.S. Application Data

(60) Provisional application No. 61/588,565, filed on Jan. 19, 2012.

(51) Int. Cl.
| | |
|---|---|
| A61B 3/00 | (2006.01) |
| A61B 3/10 | (2006.01) |
| A61B 3/107 | (2006.01) |
| G01B 9/02 | (2006.01) |
| G01N 21/47 | (2006.01) |

(52) U.S. Cl.
CPC ............... *A61B 3/102* (2013.01); *A61B 3/0025* (2013.01); *A61B 3/107* (2013.01); *G01B 9/02077* (2013.01); *G01B 9/02083* (2013.01); *G01B 9/02091* (2013.01); *G01N 21/4795* (2013.01)

(58) Field of Classification Search
USPC .................................................. 351/212, 246
See application file for complete search history.

(56) References Cited

U.S. PATENT DOCUMENTS

| | | | |
|---|---|---|---|
| 4,937,526 A | 6/1990 | Ehman et al. | |
| 5,471,303 A | 11/1995 | Ai et al. | |

(Continued)

FOREIGN PATENT DOCUMENTS

| | | |
|---|---|---|
| EP | 0697611 A2 | 2/1996 |
| WO | 03/082162 A2 | 10/2003 |
| WO | 03/105678 A2 | 12/2003 |
| WO | 2004/055473 A1 | 7/2004 |
| WO | 2007/143111 A2 | 12/2007 |

OTHER PUBLICATIONS

Boer et al., "Improved Signal-To-Noise Ratio in Spectral-Domain Compared with Time-Domain Optical Coherence Tomography", Optics Letters, vol. 28, No. 21, Nov. 1, 2003, pp. 2067-2069.

(Continued)

*Primary Examiner* — Jordan Schwartz
(74) *Attorney, Agent, or Firm* — Morrison & Foerster LLP

(57) ABSTRACT

Systems and methods for enhanced accuracy in optical coherence tomography imaging of the cornea are presented, including approaches for more accurate corneal surface modeling, pachymetry maps, keratometric values, and corneal power. These methods involve new scan patterns, an eye tracking mechanism for transverse motion feedback, and advanced motion correction algorithms. In one embodiment the methods comprise acquiring a first sparse set of data, using that data to create a corneal surface model, and then using the model to register a second set of denser data acquisition. This second set of data is used to create a more accurate, motion-corrected model of the cornea, from which pachymetry maps, keratometric values, and corneal power information can be generated. In addition, methods are presented for determining simulated keratometry values from optical coherence tomography data, and for better tracking and registration by using both rotation about three axes and the corneal apex.

28 Claims, 10 Drawing Sheets

(56) References Cited

U.S. PATENT DOCUMENTS

| | | | |
|---|---|---|---|
| 5,644,642 | A | 7/1997 | Kirschbaum |
| 6,325,512 | B1 | 12/2001 | Wei |
| 6,501,551 | B1 | 12/2002 | Tearney et al. |
| 6,552,796 | B2 | 4/2003 | Magnin et al. |
| 6,556,853 | B1 | 4/2003 | Cabib et al. |
| 6,726,325 | B2 | 4/2004 | Xie et al. |
| 6,736,508 | B2 | 5/2004 | Xie et al. |
| 6,769,769 | B2 | 8/2004 | Podoleanu et al. |
| 6,788,421 | B2 | 9/2004 | Fercher et al. |
| 6,927,860 | B2 | 8/2005 | Podoleanu et al. |
| 7,072,047 | B2 | 7/2006 | Westphal et al. |
| 7,113,818 | B2 | 9/2006 | Podoleanu et al. |
| 7,133,137 | B2 | 11/2006 | Shimmick |
| 7,145,661 | B2 | 12/2006 | Hitzenberger |
| 7,364,296 | B2 * | 4/2008 | Miller et al. ............ 351/206 |
| 7,365,856 | B2 | 4/2008 | Everett et al. |
| 7,480,059 | B2 * | 1/2009 | Zhou et al. ............ 356/498 |
| 7,512,436 | B2 | 3/2009 | Petty et al. |
| 7,699,468 | B2 | 4/2010 | Gaida |
| 7,755,769 | B2 | 7/2010 | Everett et al. |
| 8,018,598 | B2 | 9/2011 | Cense et al. |
| 8,115,935 | B2 | 2/2012 | Everett et al. |
| 2002/0085208 | A1 | 7/2002 | Hauger et al. |
| 2003/0103212 | A1 | 6/2003 | Westphal et al. |
| 2003/0199769 | A1 | 10/2003 | Podoleanu et al. |
| 2003/0227631 | A1 | 12/2003 | Rollins et al. |
| 2005/0140984 | A1 | 6/2005 | Hitzenberger |
| 2005/0219544 | A1 | 10/2005 | Chan et al. |
| 2006/0228011 | A1 * | 10/2006 | Everett et al. ............ 382/128 |
| 2012/0140175 | A1 | 6/2012 | Everett et al. |
| 2012/0249956 | A1 * | 10/2012 | Narasimha-Iyer et al. ... 351/206 |
| 2014/0241605 | A1 * | 8/2014 | Izatt et al. ............ 382/131 |

OTHER PUBLICATIONS

Choma et al., "Sensitivity Advantage of Swept Source and Fourier Domain Optical Coherence Tomography", Optics Express, vol. 11, No. 18, Sep. 8, 2003, pp. 2183-2189.

Ehman et al., "Adaptive Technique for High-Definition MR Imaging of Moving Structures", Radiology, vol. 173, No. 1, Oct. 1989, pp. 255-263.

Hammer et al., "Active Retinal Tracker for Clinical Optical Coherence Tomography Systems", Journal for Biomedical Optics, vol. 10, No. 2, Mar./Apr. 2005, pp. 024038-1-024038-11.

Hitzenberger et al., "Three-Dimensional Imaging of the Human Retina by High-Speed Optical Coherence Tomography", Optics Express, vol. 11, No. 21, Oct. 20, 2003, pp. 2753-2761.

Huang et al., "Optical Coherence Tomography", Science, vol. 254, Nov. 22, 1991, pp. 1178-1181.

Joergensen et al., "Reducing Speckle Noise in Retinal OCT Images by Aligning Multiple B-Scans", Coherence Domain Optical Methods and Optical Coherence Tomography in Biomedicine VIII, Proceedings of the SPIE, vol. 5316, 2004, pp. 205-213.

Leitgeb et al., "Performance of Fourier Domain vs. Time Domain Optical Coherence Tomography", Optics Express, vol. 11, No. 8, Apr. 21, 2003, pp. 889-894.

Nassif et al., "In Vivo High-Resolution Video-Rate Spectral-Domain Optical Coherence Tomography of the Human Retina and Optic Nerve", Optics Express, vol. 12, No. 3, Feb. 9, 2004, pp. 367-376.

Non Final Office Action received for U.S. Appl. No. 12/794,926, mailed on Apr. 4, 2011, 10 pages.

Notice of Allowance received for U.S. Appl. No. 12/075,477, mailed on Mar. 8, 2010, 7 pages.

Notice of Allowance received for U.S. Appl. No. 12/794,926, mailed on Oct. 11, 2011, 9 pages.

Non-Final Office Action received for U.S. Appl. No. 13/357,097, mailed on Sep. 12, 2013, 9 pages.

International Search Report and Written Opinion received for PCT Patent Application No. PCT/EP2013/000152, mailed on Jun. 27, 2013, 16 pages.

Invitation to Pay Additional Fees received for PCT Patent Application No. PCT/EP2013/000152, mailed on May 3, 2013, 5 pages.

Notice of Allowance received for U.S. Appl. No. 13/357,097, mailed on Dec. 17, 2013, 10 pages.

Everett et al., Unpublished U.S. Appl. No. 14/242,683, filed Apr. 1, 2014, titled "Method of Motion Correction in Optical Coherence Tomography Imaging".

* cited by examiner

SYSTEMS AND METHODS FOR ENHANCED ACCURACY IN OCT IMAGING OF THE CORNEA

PRIORITY

This application claims the benefit of the filing date under 35 U.S.C. §119(e) of Provisional U.S. Patent Application Ser. No. 61/588,565, filed on Jan. 19, 2012, which is hereby incorporated by reference in its entirety.

FIELD OF THE INVENTION

The present invention relates to medical imaging, and in particular data acquisition and processing methods for data acquired through optical coherence tomography (OCT).

BACKGROUND

Optical coherence tomography (OCT) is an optical imaging technology for performing in situ real-time cross-sectional imaging of tissue structures at a resolution of less than 10 microns. OCT measures the scattering profile of a sample along the OCT beam. Each scattering profile is called an axial scan, or A-scan. Cross-sectional images, called B-scans, and by extension 3D volumes, are built up from many A-scans, with the OCT beam moved to a set of transverse locations on the sample.

In recent years, it has been demonstrated that Fourier domain OCT (FD-OCT) has advantages over the original time-domain OCT (TD-OCT) (R. A. Leitgeb et al. (2003). "Performance of fourier domain vs. time domain optical coherence tomography." Optics Express 11(8): 889-94; J. F. de Boer et al. (2003). "Improved signal-to-noise ratio in spectral-domain compared with time-domain optical coherence tomography." Optics Letters 28(21): 2067-2069; M. A. Choma et al. (2003). "Sensitivity advantage of swept source and Fourier domain optical coherence tomography." Optics Express 11(18): 2183-89). In TD-OCT, the optical path length between the sample and reference arms needs to be mechanically scanned. In FD-OCT, on the other hand, the optical path length difference between the sample and reference arm is not mechanically scanned. Instead, a full A-scan is obtained in parallel for all points along the sample axial line within a short time, determined by the wavelength sweep rate of a swept source in swept-source OCT (SS-OCT) or the line scan rate of the line scan camera in spectral-domain OCT (SD-OCT). As a result, the speed for each axial scan can be substantially increased as compared to the mechanical scanning speed of TD-OCT.

Even with the increased speed of FD-OCT, however, the accuracy of OCT for a number of ophthalmic applications can be limited by the effect of motion during data acquisition. These applications include pachymetry, keratometry, and corneal power calculations.

Pachymetry

Pachymetry is the measurement of corneal thickness. Corneal thickness can be important in assessing corneal diseases, intraocular pressure, ocular hypertension, and a patient's eligibility for refractive surgical procedures (Y. Li et al. (2010). "Pachymetric mapping with Fourier-domain optical coherence tomography." J. Cataract Refract. Surg. 36(5): 826-31, hereby incorporated by reference). The use of optical coherence tomography (OCT) to generate pachymetry maps has been well demonstrated using both time-domain and Fourier-domain OCT systems (see for example Y. Li et al. (2010).). Pachymetry maps are generated by calculating the corneal thickness along each of these scans. It is desirable to obtain high density pachymetry maps by either acquiring more meridional scans, or by sampling the cornea more densely, as it minimizes the probability of missing smaller regions of pathology. However, denser sampling would require a longer scan time, and would, in turn, make the data more susceptible to eye motion. A method for generating a denser pachymetry map without motion-related error would therefore be desirable.

Keratometry

Keratometry is the measurement of the curvature of the anterior surface of the cornea. A number of different instrument types can be used to determine the curvature. Often, measurements are taken not by true keratometers but by corneal topographers, which provide simulated keratometry (Sim-K) readings. These do not directly measure the x, y, and z coordinates of the points on the corneal surface, but instead generally use the reflection of incident light by the cornea to measure its shape. The most popular type of modern corneal topographer is the Placido system, which projects multiple light concentric rings on the cornea. The reflection is captured, and then the height of each point of the cornea is extrapolated from the reflection. Computer software and algorithms can analyze the data and display the results in various maps; typically they measure the deviation of reflected rings and calculate the curvature of the corneal surface points in the axial direction, which can then be used to compute Sim-K.

Sim-K measurements characterize curvatures in the central 3 mm area of the cornea. The measurements are essentially what a manual keratometer would estimate the corneal curvature to be at approximately the 3 mm zone. The measurements generated by simulated keratometry include the curvature and axes of the steepest and flattest meridians of the cornea. The steep Sim-K is the steepest meridian of the cornea, based on samples along the central pupil area with 3-mm diameter. The flat Sim-K is the flattest meridian of the cornea and is by definition 90° apart from the steepest meridian. These readings provide the central corneal curvature that is visually most significant. Sim-K is valuable for detection of postoperative astigmatism, planning of removal of sutures, and postoperative fitting of contact lenses.

Corneal topography, however, has certain limitations. For example, it requires an intact epithelial surface and tear film to neutralize corneal irregularities. Also, error can arise from problems caused by misalignment and fixation error that amplify measurements of astigmatism, which decreases the accuracy of the corneal measurements. It can also be difficult to calculate the position of the center from the small central rings, and there can be increased inaccuracy toward the periphery because the accuracy of each point depends on the accuracy of all preceding points.

Under optimal conditions, the error of corneal topography is around ±0.25 D. However, the errors can be significantly higher in abnormal corneas—often ±0.50-1.00 D (see for example A. K. Gupta (2012). *Clinical Ophthalmology: Contemporary Perspectives*). Thus, there is a need for a method of measuring the curvature of the cornea with greater accuracy, especially in abnormal corneas. Although OCT is currently being used to calculate net central corneal power (see D. Huang (2012). "Corneal power and IOL power calculation with OCT," presentation to Taiwan Academy of Ophthalmology, available at http://www.coollab.net/fileadmin/coollab_upload/coollab/docs/1Huang-OCT-based_IOL_formula-taiwan.pdf), the methods described here would allow additional metrics to be determined as well, which may be useful for refractive surgery planning. This method may also allow existing formulas for intraocular lens (IOL) power calculation (see for example K. J. Hoffer (1993). The Hoffer Q formula: a comparison of theoretic and regression formulas. J. Cataract Refract. Surg. 19(6): 700-12) to be used, since the corneal power is calculated by similar models as those in existing devices such as IOL Master (Carl Zeiss Meditec, Inc. Dublin, Calif.).

Corneal Power

Accurate measurement of corneal power is essential for various diagnostic and therapeutic applications in ophthalmology. Standard keratometers determine posterior corneal power by extrapolating based on the assumption of a fixed keratometric index, which is in turn based on the assumption of a fixed ratio between anterior and posterior curvature. This assumption of a fixed ratio leads often to incorrect results when changes in surface curvature occur mostly at the anterior corneal surface—for instance, due to pathology or refractive surgery. This assumption can thus lead to incorrect corneal power determinations (M. Tang et al. (2010). "Corneal power measurement with Fourier-domain optical coherence tomography." J. Cataract Refract. Surg. 36(12): 2115-22).

Instead of manual or simulated keratometry, OCT data can be used to determine corneal power. Using two-dimensional OCT cross-sectional scans to determine corneal power by measuring the radius of curvature of anterior and posterior corneal surfaces has been suggested and demonstrated (see, for example, M. Tang et al. (2010); U.S. Pat. No. 7,878,651 to O'Hara et al.). Existing methods calculate corneal power by using least squares to determine a parabolic fit to each meridional scan over the central 3 mm diameter area. The powers of each meridian are then averaged to obtain the anterior, posterior, and net corneal powers.

One of the biggest challenges, however, in using OCT B-scans for calculating the corneal power is the error in curvature measurements caused by motion of the cornea in the z and transverse directions. Small movements can cause significant errors in power calculations. For example, a z displacement of 1.3 µm while the scan beam moves 1 mm from the vertex will result in error of approximately 1 diopter in corneal power. O'Hara et al. suggest techniques for z-motion correction by using Doppler signal and by measuring displacement of a single point during repeated scans. However, any translational movement of the pupil may reduce the effectiveness of the z-correction. It is true that the effect of translational motion perpendicular to the B-scan direction would cause errors of relatively lower magnitude. Nonetheless, the effect for lateral motion cannot be neglected for high accuracy measurements of corneal curvature. Even at the vertex, where the lens sag due to transverse motion is at a minimum, a displacement of 200 µm could cause an error of approximately 1.84 diopters in measurements. This error will only increase with greater distance from the vertex of the cornea.

The power computation may also be inaccurate in corneas with pathology or after refractive surgery. In these cases, the corneal surface in the 3 mm diameter region may not be modeled accurately using a parabolic model fit. Therefore, a robust and accurate fitting method is essential for accurate corneal power computation. Thus, although OCT is capable of directly measuring both corneal surfaces, a method of using OCT for corneal power measurements that has acceptable accuracy and repeatability is desirable.

Tracking and Registration

Active and accurate corneal surface tracking and registration are important for the applications described here. Accurate change analysis of measurements from multiple visits (e.g. before and after corneal surgery) is essential for comparing the difference in pachymetry or epithelial maps. Thus, accurate corneal surface registration becomes an inevitable preprocessing step in the change analysis. Also, axial curvature maps (from multiple visits) that determine the radius of curvature of the cornea at each measured point, and resulting Sim-k values, as well as corneal power calculations, will not be repeatable and comparable between different visits without proper registration. Tracking and registration can also be incorporated into an efficient alignment of OCT-based acquisition systems, improve the repeatability of anterior segment measurement, and enhance laser eye surgery systems and techniques by aiming to reduce the effect of patient eye movement.

Existing tracking methods for OCT systems generally involve locating an iris, pupil center, a corneal vertex, and/or at least one reflection on the image. A computer processor having a program computes the position of the iris or pupil center on an image of the eye, or the position of a corneal vertex from a series of OCT B-scans. Like existing tracking methods, existing registration methods involve using the pupil or corneal vertex as the centration landmark. These methods are problematic because the corneal vertex depends on the eye's fixation to a specific target. Orientation of the corneal surface also depends on the eye's fixation to a specific target, but these techniques neglect the eye's rotation around three axes. Thus, there is a need for tracking and registration methods that take the corneal surface rotation about three axes into consideration and that rely on a fixed position on the corneal surface. One such fixed position whose use as a reference point would improve tracking and registration is the corneal apex.

SUMMARY

Here we propose several approaches for enhancing the accuracy in the calculation of ocular measurements, including anterior segment measurements such as corneal surface modeling, pachymetry maps, keratometric values, and corneal power using OCT. These methods involve the generation of new scan patterns, the use of an eye tracking mechanism for transverse motion feedback, and the application of advanced motion correction algorithms.

More specifically, we propose a method comprising acquiring a first sparse set of data using an OCT system, and then using that data to create a surface model of the cornea. This surface model can be used to register a second set of denser data acquisition. From this second set of data, a second, more accurate motion-corrected model of the cornea can be created. This motion-corrected model can then be used to generate measurements including pachymetry maps, keratometric values, and corneal power information with enhanced accuracy.

We also propose a method of determining sim-K from OCT data. Even if future OCT systems provide an ultra high-speed scan of the corneal surface with almost motion artifact-free scans that can be used to reconstruct the corneal model, the methods described here could still be used to determine keratometric values and be used for topographic diagnosis of various diseases by accurately generating various topographic maps and biometric values.

Corneal power measurements with enhanced accuracy can also be generated from a set of dense B-scans using the anterior and posterior curvature information, together with knowledge of the corneal and aqueous humor refractive indices. The corneal power measurements generated using the method described here have enhanced accuracy due to a number of factors, including allowing for multiple scans, accounting for eye motion, improved anterior and posterior segmentation, increased accuracy of corneal vertex position, using Random Sample Consensus (RANSAC) robust fitting, using calibration parameters for beam geometry correction, and calibration of the OCT system.

In addition, the methods described here can be used for better tracking and registration by using both rotation about three axes and the corneal apex. Rather than registering or tracking a specific feature on a corneal surface, one embodiment of this invention tracks or registers the corneal surface as a whole by creating a corneal model and detecting the corneal apex position and orientation of the anterior or posterior corneal surface about three axes. This method takes advantage of the fact that the general shape of cornea is a quadric surface. The corneal model can be estimated using a robust fit to exclude outliers, such as pathology, interferences, or motion. Using the apex position along with principle axes of the corneal surface can lead to more accurate corneal surface registration and tracking.

Although the methods in this patent are focused primarily on applications in the cornea, it will be apparent to someone skilled in the art that the rest of the eye may be represented by a model and therefore measurements of other ocular structures, including other anterior segment structures, the lens of the eye, and posterior structures in the eye may benefit from the methods described in this patent.

DETAILED DESCRIPTION

Figure 1:
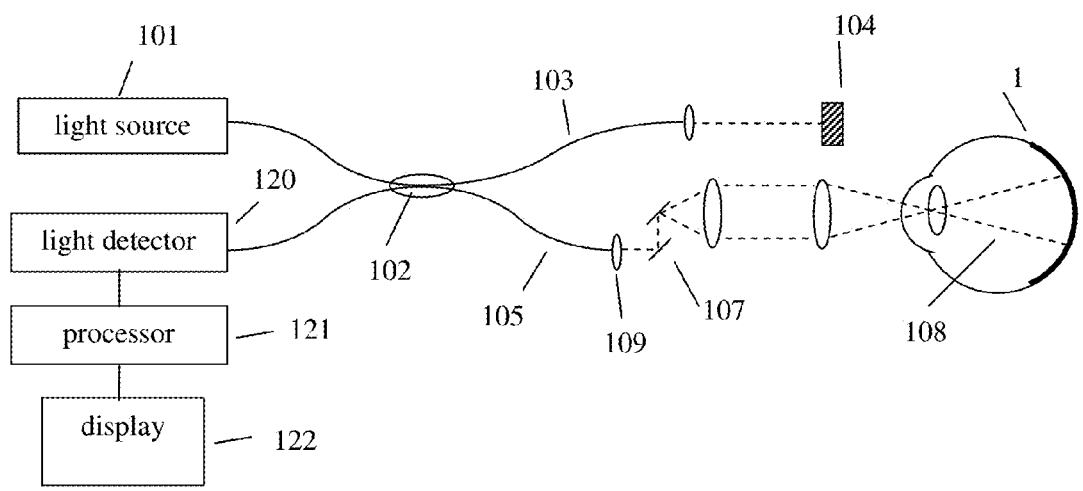
FIG. 1 is a diagram of a generalized frequency-domain OCT system for use in ophthalmology.

A diagram of a generalized frequency-domain OCT (FD-OCT) system for use in ophthalmology is shown in FIG. 1. Light from source 101 is routed, typically by optical fiber 105, to illuminate the sample 110, a typical sample being tissue in the human eye. Typical sources are a broadband light source with short temporal coherence length in the case of spectral-domain OCT (SD-OCT), or a wavelength-tunable laser source in the case of swept-source OCT (SS-OCT). The beam of light (dashed line 108) is scanned laterally (in x and y, if z is parallel to the beam of light) over the area or volume to be imaged, typically with scanning optics 107 between the output of the fiber and the sample. Light backreflected from the sample returns through scanning optics 107 and is collected, typically into the same fiber 105 used to route the light for sample illumination. Lens 109 is used to collimate the illuminating light exiting the fiber and to focus the reflected light back into the fiber for collection. Reference light derived from the same source 101 travels a separate path, in this case involving fiber 103 and retro-reflector 104 with an adjustable optical delay. Those skilled in the art will recognize that a transmissive reference path can also be used and that the adjustable delay could be placed in either the sample or reference arm of the interferometer. Additionally, the interferometer could consist of fiber optics, bulk optical components, or a combination thereof. Collected sample light is combined with reference light, typically in a fiber coupler 102, to form light interference in a detector 120. Although a single fiber port is shown going to the detector, those skilled in the art will recognize that various designs of interferometers can be used for balanced or unbalanced detection of the interference signal. The output from the detector is supplied to a processor 121. The results can be stored in the processor 121 or displayed on display 122.

The interference between the light returning from the sample and from the reference arm causes the intensity of the interfered light to vary across the spectrum. The Fourier transform of the interference light reveals the profile of scattering intensities at different path lengths, and therefore scattering as a function of depth (z-direction) in the sample (see for example R. Leitgeb et al. (2004). "Ultrahigh resolution Fourier domain optical coherence tomography." Optics Express 12(10): 2156-65). The scattering profile as a function of depth is called an axial scan (A-scan). A set of A-scans measured at neighboring locations in the sample produces a cross-sectional image (tomogram or B-scan) of the sample. A collection of B-scans makes up a data cube or cube scan. It should be noted, however, that the application of these methods need not be limited to data acquired via FD-OCT; they could also be applied to data acquired via TD-OCT.

Corneal Surface Modeling

Figure 2:
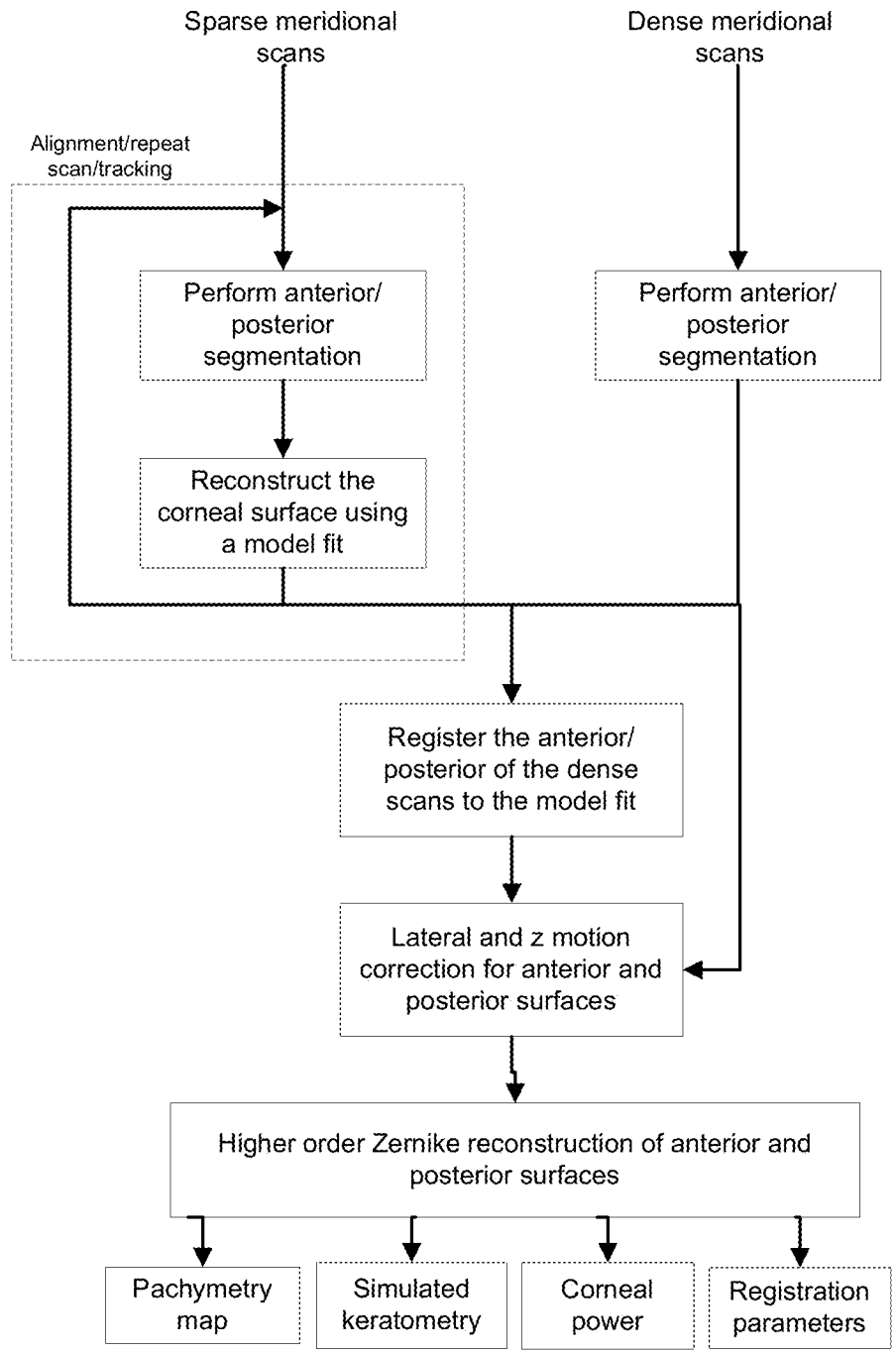
FIG. 2 is a flow diagram of the algorithm from acquiring meridional sparse and dense scans to pachymetry mapping, keratometry mapping, corneal power computation, or registration parameter calculation.

FIG. 2 shows the method for creating a model of the cornea. Data acquisition is divided into two parts: a first sparse scan pattern that is used to create an initial model of the cornea, and a second dense scan pattern.

The first part of the data acquisition is the sparse scan, in which a set of B-scans of the cornea are acquired. These are acquired in a relatively short amount of time—within a time period of few hundred milliseconds or less. Because they are acquired during this short time span, the effect of motion is minimal, and thus they are generally free from any significant motion and tilt variations during the acquisition of the scan. (For further discussion of the time period in which OCT data must be acquired to avoid objectionable eye motion, see U.S. Pat. No. 7,365,856 to Everett et al. "Method of motion correction in optical coherence tomography imaging," herein incorporated by reference.) The sparse scan pattern could comprise any number or shape of scans (meridional or radial, circular, spiral, or other patterns) that can be completed within a time short enough to avoid any significant amount of motion while providing adequate data to generate for the following steps in the method. In a preferred embodiment, this initial set of B-scans consists of eight perpendicular meridional B-scans.

These B-scans are then segmented to identify either the anterior or posterior layer of the cornea. One effective way of segmenting the B-scans takes advantage of the fact that the general shape of the cornea can be modeled as a quadric surface. Initial estimates of the anterior and posterior layers are first identified. To estimate initial position of anterior and posterior surface, a normalized cross-correlation is performed between each A-scan and two functions. The first function represents the approximate transition from air to stroma and the second function represents the approximate transition from stroma to aqueous humor. The positions with the highest normalized cross-correlation values are recorded as the initial estimate of the anterior or posterior surface. A corneal layer in a 2-D B-scan can be assumed to be a conic section (parabola, ellipse, hyperbola, etc.). We fit a parabola to the initial estimated values using RANSAC, a method described in more detail below, by robustly estimating the parameters of parabola from the data which contains outliers.

The final estimates of layer position are then found using the hybrid graph theory and dynamic programming framework (see S. Timp et al. (2004). "A new 2D segmentation method based on dynamic programming applied to computer aided detection in mammography." Medical Physics 31(5): 958-971, hereby incorporated by reference). In this method, the parabola fitted to the initial estimated values is used to define a region of interest (ROI) as the region around this parabola. After an ROI containing a layer (anterior or posterior) is identified, the graph-based segmentation can be performed within the ROI.

If there is specular reflection, this can be removed. Specular reflection has relatively high intensity in a set of A-scans in the central region of the cornea. Identifying the specular reflection position is crucial for accurate corneal power calculation and pachymetry map generation. The anterior/posterior points in the specular reflection region will be removed before corneal power and pachymetry computation. A projection of the B-scan is performed to generate a 1-D data which is used for specular reflection detection. The generated 1-D data can be interpreted as a Gaussian type of function. We fit a Gaussian function to the data. The normalized cross correlation coefficient between the Gaussian function and the data will be a metric to determine whether the specular reflection occurs in the B-scan.

A two-dimensional surface model is then fitted to these layers. Because of the minimal motion during acquisition, the fit is essentially motion-free. In a preferred embodiment, the model can be a quadric or Zernike polynomial, generally of a lower order. One method by which the model parameters may be determined is a robust fitting method, such as RANSAC fitting, which is described in more detail below. This model forms the initial estimate of the corneal surface.

The second part of the data acquisition, the dense scan, samples the cornea more densely. The sampling may be denser with respect to the number of A-scans per B-scan, the total number of B-scans, the number of pixels per A-scan, or all three. The data acquisition time could be longer by a factor of two or more compared to the first sparse scan. Because the denser set of data takes longer to acquire, unlike the initial sparse scan, it likely is affected by motion. Again, any number of or shape of scans could be used (meridional or radial, circular, spiral, or other patterns). The next steps involve using the initial estimate of the corneal surface generated from the first sparse scan to correct the dense scan for motion. First, a B-scan from the dense scan can be segmented to identify the anterior or posterior layer. The segmentation can be carried out through the same method using a dynamic programming framework described above. Then, the lateral and z-displacement caused by the eye motion can be detected by registering the segmented layer to the model generated from the sparse scan. The anterior or posterior layer can be registered to the model in any suitable way, but one example is to find the corresponding section of the model by solving the minimization problem:

$$\operatorname*{argmin}_{A} \sum_{i} \|AW_i - V_i\|^2$$

where
$W_i = [x, y, z]^T$ and x, y, and z are the coordinates of a meridional anterior or posterior layer at a given point;
$V_i = [x, y, z]^T$ and x, y, and z are the coordinates of a conic section at a given point; and
A is a transformation matrix.

By solving this minimization problem, the lateral and z-motion of the cornea can be corrected for. Other approaches to register the new B-scan to the model could also be used, including minimizing other mathematical functions.

Each B-scan in the dense set can be registered to the initial model as described above. Alternatively, after each B-scan in the dense set is registered to the model, a new model can be created using all of the B-scans already in the model plus the new B-scan. In this way, the model can be iteratively updated as additional B-scans are registered. In addition, the registration method could be modified in other ways as well. For instance, rather than registering individual B-scans to the model, pairs of perpendicular B-scans could be registered to the model as a pair. In some variations, the method can also include determining which scans in the dense set had appreciable motion and excluding them from further analysis.

The motion-corrected set of dense scans can then be used to create a model of the anterior and/or posterior surfaces of the cornea. Modeling the corneal surface is essential for certain anterior segment applications. One way of modeling the corneal surface that is particularly helpful is the Zernike polynomial. This type of polynomial is good for representing the corneal shape and provides an accurate solution when the underlying surface is relatively smooth and motion free. For certain applications, such as keratometry, the $7^{th}$ order Zernike polynomial that gives 36 Zernike coefficients adequately approximates the corneal surface. The discrete set of data points in polar coordinate system are expanded into Zernike polynomials such that $$z(\rho_i, \theta_i) = \sum_{n, \pm m} a_{n, \pm m} Z_n^{\pm m}(\rho_i, \theta_i)$$

for all points $(\rho_i, \theta_i)$. $Z_n^{\pm m}(\rho_i, \theta_i)$ is the Zernike polynomial and $\{a_{n \pm m}\}$ are the Zernike coefficients. In some cases, the coefficients may be determined using a robust fitting algorithm, such as Random Sample Consensus (RANSAC) fitting, which is explained in more detail below.

Once a model of the cornea is created from the dense set of scans, the method can be extended to use the model for additional applications. These include obtaining highly accurate and dense pachymetry maps with minimal motion artifacts, keratometric values, and corneal power measurements.

Pachymetry Maps

The model of the cornea can be used to generate high density and motion-artifact free pachymetry maps. When generating pachymetry maps, both the anterior and posterior surfaces are modeled using the motion-corrected set of dense scans, as described above. The pachymetry values are then based on the corneal thickness, which is defined as the closest distance from each anterior surface point to the posterior surface. In one embodiment, this distance can be calculated using the fast marching distance transform (see A. Telea (2004). "An image inpainting technique based on the fast marching method." Journal of Graphics Tools 9(1): 25-36, hereby incorporated by reference). In one variation, the pachymetry maps can be based on fitting Zernike polynomials to the corneal anterior and posterior surfaces from twenty-four meridional scans.

The pachymetry map can also be generated from thickness measurements from individual dense B-scans, which are then combined to form a map. To do so, after the anterior and posterior layers are segmented in each B-scan, instead of using a surface model of the layers to determine thickness, the thickness is calculated for each B-scan individually. The thickness is measured as the distance from the anterior surface to the closest point of the posterior surface in the B-scan. In the case of meridonal scans, the thickness values from the individual B-scans are then combined to create a sparse polar map. This can then be converted to a 2-D Cartesian map using a 2-D interpolation method such as grid-fit to approximate the 2-D pachymetry map (see for example J. R. D'Errico (2006). *Understanding Gridfit*). Polar to Cartesian map conversion is a fitting of the form z(x, y) to polar data. Grid fit can also fit a surface to scattered (or regular) data. The fitting method should produce a surface that represents the behavior of the data as closely as possible, allowing for noise in the data and for replicate data.

Figure 3:
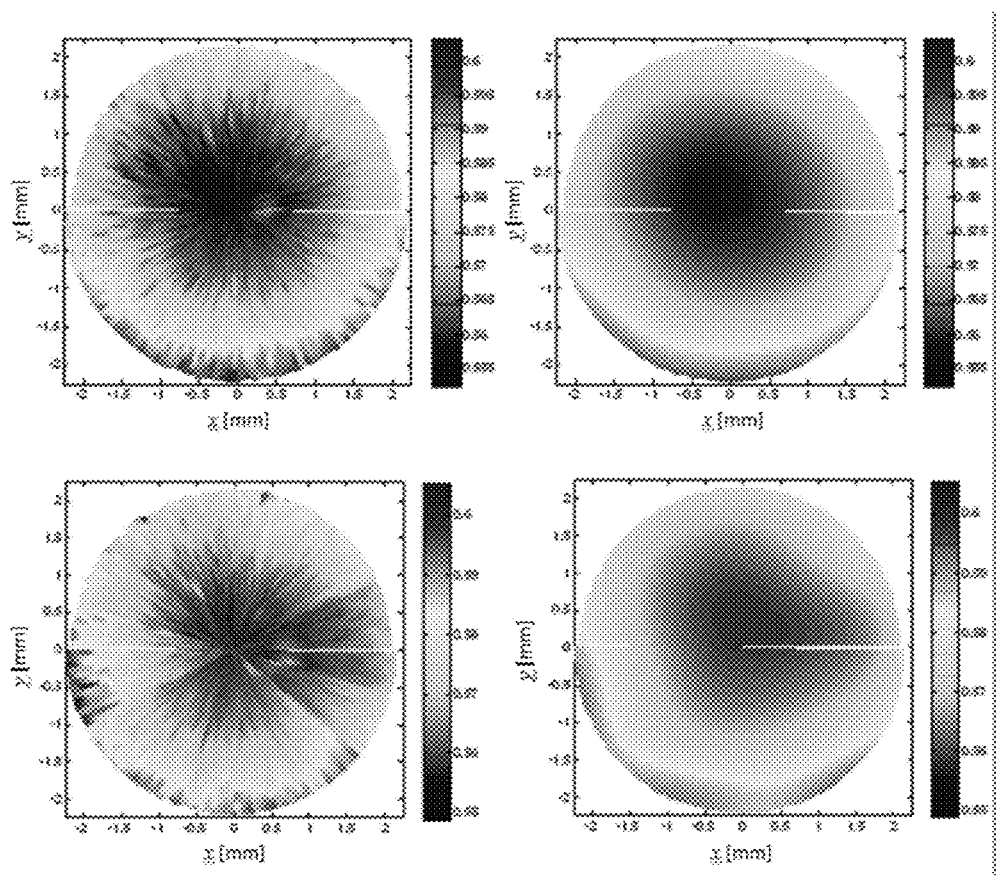
FIG. 3 shows pachymetry maps generated before and after motion correction.

FIG. 3 shows pachymetry maps in two cases generated from combining thickness measurements from individual B-scans. The left shows maps generated from a dense scan without motion correction, and the rights shows maps generated from a dense scan with motion correction by registering the dense scans to the initial model.

Simulated Keratometry

Another extension of the corneal surface modeling method described here is the computation of corneal curvature based only on OCT data. In contrast to corneal topographers, OCT systems directly measure the x, y, and z coordinates of the points on the corneal surface. After the OCT data is used to construct a corneal surface model as described above, an axial curvature map of the corneal surface can be created by computing the axial curvatures at all surface points.

Figure 4:
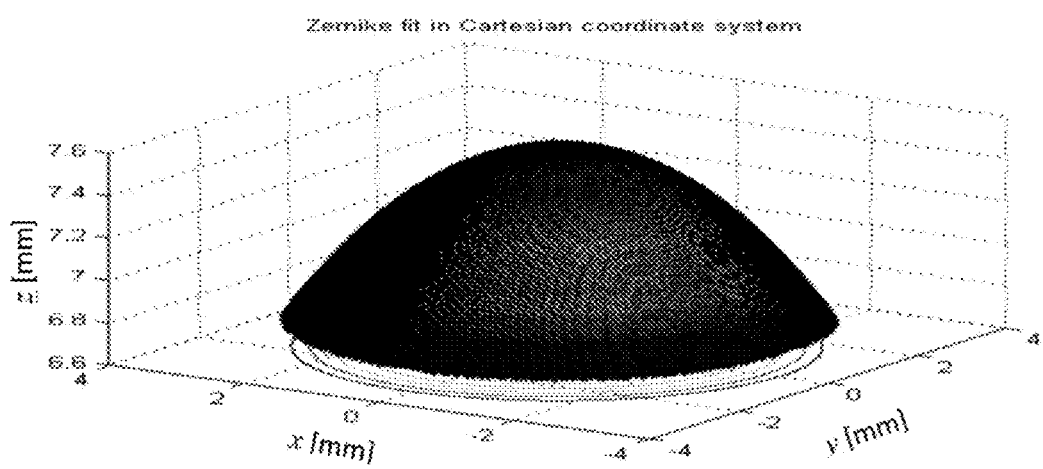
FIG. 4 shows a corneal surface originally represented by a Zernike polynomial resampled in Cartesian coordinates.

First, as shown in FIG. 4, if the corneal surface model is in the polar coordinate system, the corneal surface is re-sampled using the set of coefficients $\{a_{n,\pm m}\}$ to create a uniform and equidistance sampling of the corneal surface in the x and y directions, forming a new surface in Cartesian coordinate system.

Then the axial curvatures are calculated. The axial curvature at a given point (x,y,z) on the corneal surface is defined as the distance along the surface normal $(n_x,n_y,n_z)$ from the point of interest to the optical axis, which is assumed to intersect the vertex of the cornea.

Figure 5A:
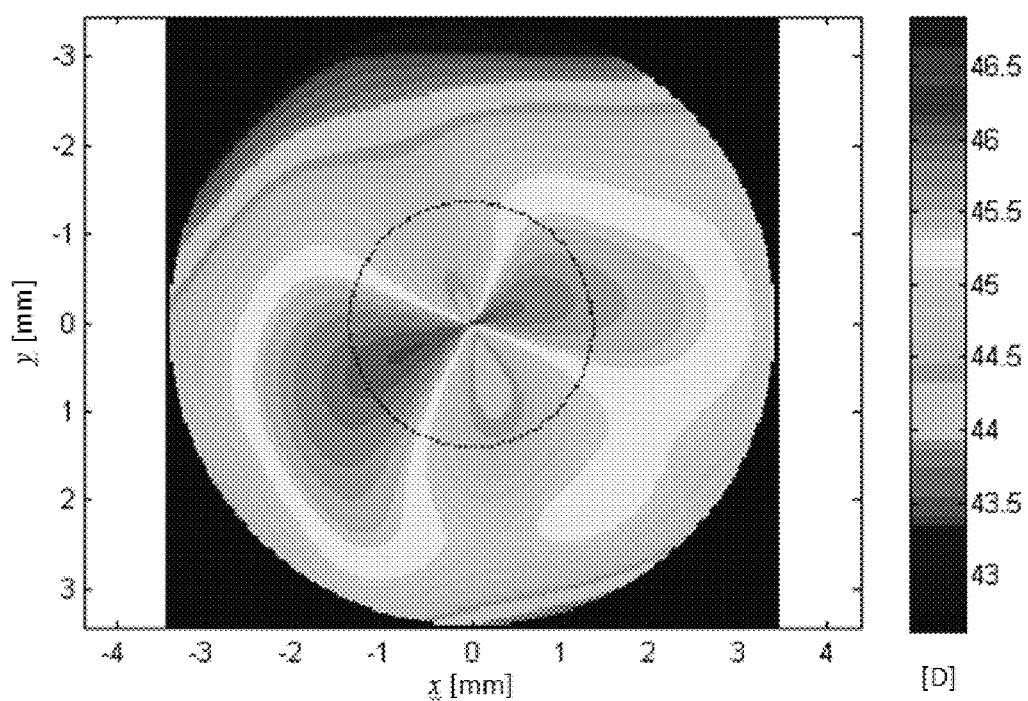
FIG. 5A is an example of an axial curvature map.
Figure 5B:
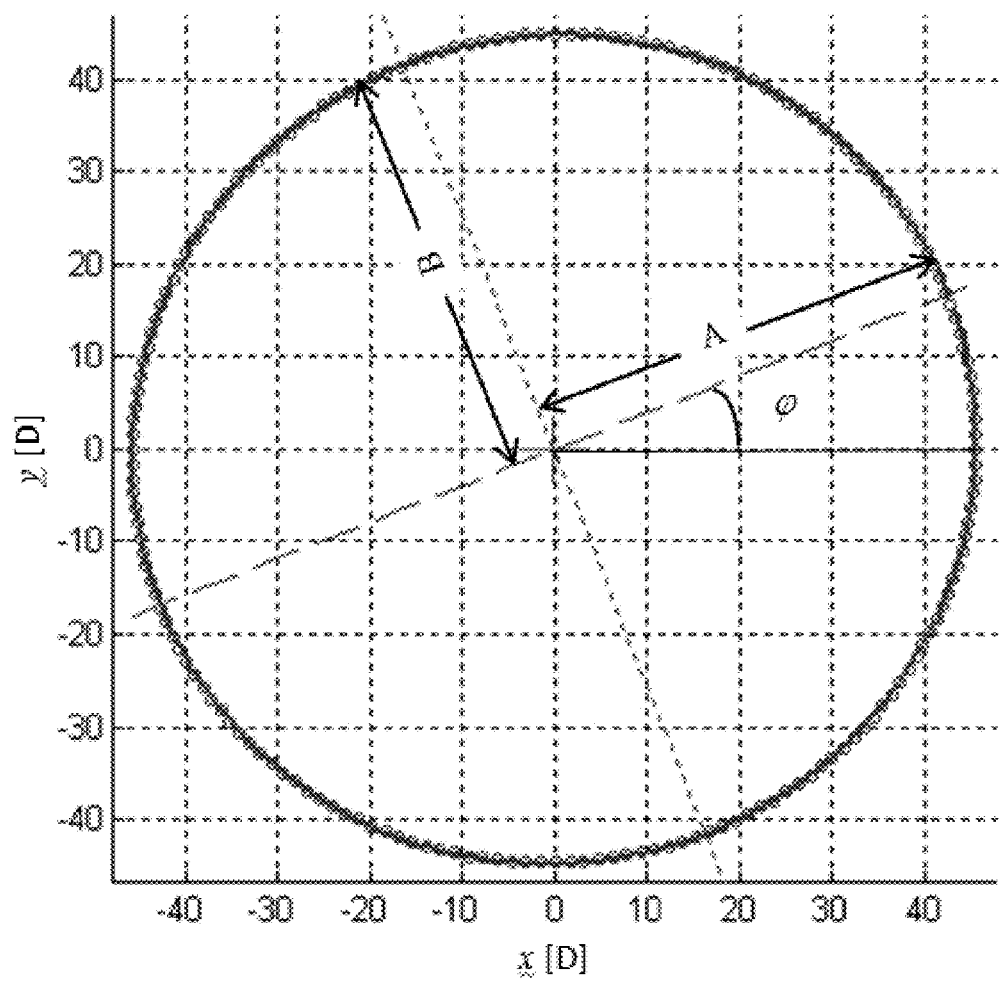
FIG. 5B is an example of sampled axial curvature data.

The Sim-K is then calculated based on sampling the axial curvature map with the x, y coordinates of corneal surface at a given zone diameter (depending on the eye shape and curvature) with the same elevation. The zone diameter can be determined for each eye based on the corneal radius/power at the vertex using the formula $$D = d/2.4 * 2 * 0.1527 * R$$

where d is a given ring measurement zone diameter (for example, 2.4 mm or 3 2 mm); and R is the corneal radius of curvature at the vertex for the nominal zone of 2.4 mm An ellipse based on the sampled axial curvature data can be generated by converting the polar (axial curvature values at sampled data in the axial curvature map represent the radiuses at the given angle) to Cartesian coordinates that provide the x and y coordinates of the ellipse at the center $(x_c, y_c)$, the major axis A and minor axis B, and the radian angle φ of the major axis with respect to the x-axis. The major axis A and minor axis B represent the steep- and flat-K respectively. The angle φ of the major axis with respect to the x-axis represents the steep-axis. An example of a resulting axial curvature map and sampled axial curvature data is illustrated in FIGS. 5A and 5B.

If the OCT data is sufficiently motion- and artifact-free, this method of calculating Sim-K from OCT data could also be carried out on a model created directly from a segmented dense scan of the cornea, rather than relying on registration to an initial model based on a sparse data set.

Corneal Power Measurements

Another extension of the corneal surface modeling method described here is the computation of corneal power. After the OCT data is used to construct a corneal surface model and to calculate anterior and posterior curvatures at the vertex, the corneal power can then also be calculated using the following equation:

$$K = K_a + K_p - D \times K_a \times K_p / n_1.$$

where $$K_a = \frac{(n_1 - n_0)}{R_a};$$

Anterior power with radius of curvature $R_a$ at the vertex $$K_p = \frac{(n_2 - n_1)}{R_p};$$

Posterior power with radius of curvature $R_p$ at the vertex

D=central corneal thickness at the vertex
$n_0$=1 Refractive index of air
$n_1$=1.386 Refractive index of cornea
$n_2$=1.333 Refractive index of aqueous humor.

As an alternative to calculating the corneal power from the corneal model created with the dense set of B-scans, a motion-corrected or motion-uncorrected dense set of B-scans can also be the basis for corneal power calculations. The total corneal power can be calculated from the anterior and posterior curvature information, together with knowledge of the corneal and aqueous humor refractive indices.

Figure 6A:
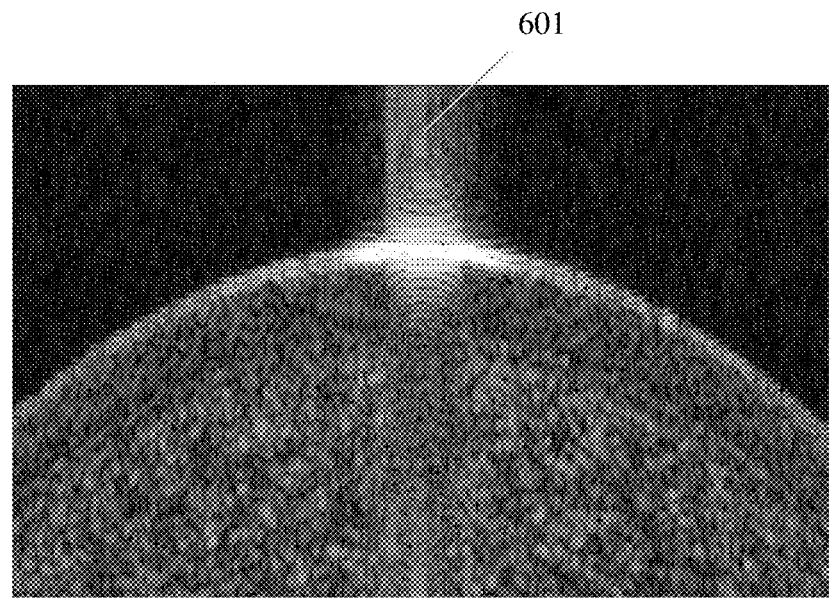
FIG. 6A is a meridional B-scan with specular reflection.
Figure 6B:
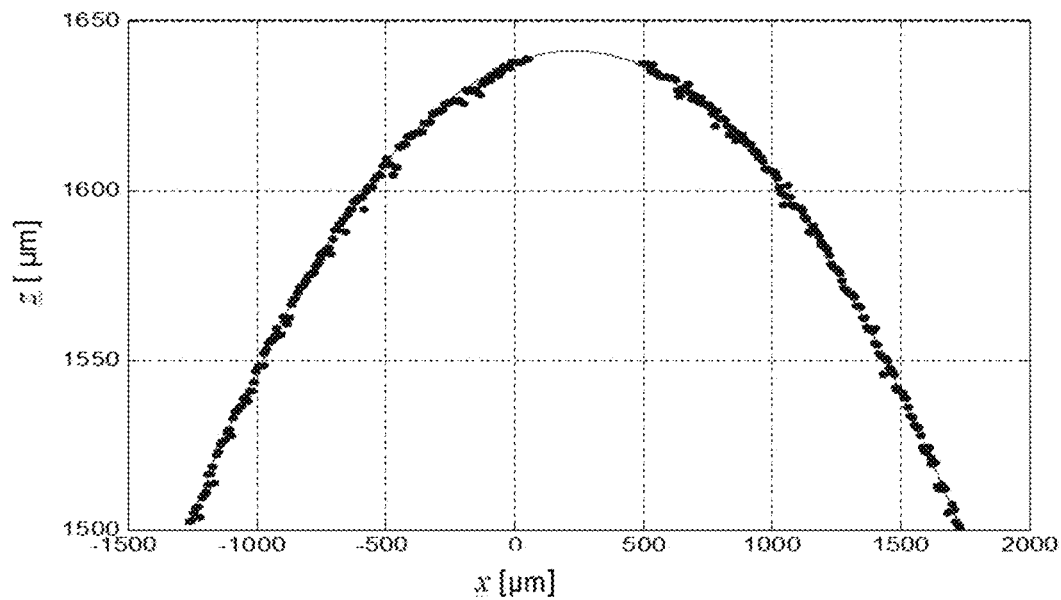
FIG. 6B shows the segmented anterior layer from the meridional B-scan of FIG. 6A, with the data points in the areas of specular reflection removed.

First, the anterior and posterior layers for each meridian in a 3 mm zone around the vertex of the anterior layer are segmented. One method by which they can be segmented is the method using a dynamic programming framework described above. If there is any specular reflection, it can be removed. FIG. 6A shows a meridional B-scan with specular reflection 601. FIG. 6B shows the segmented anterior later from this meridian, with the data points in the areas of specular reflection removed.

A fit can then be made to the anterior and posterior layers of the meridian. The method is not limited to a specific model fit, such as parabolic fit. For whichever type of fit is appropriate, the parameters may be determined using a robust algorithm: for instance, Random Sample Consensus (RANSAC) fitting. RANSAC is a technique for fitting a model to experimental data. Unlike many other techniques for parameter estimation, RANSAC assumes that the data contains data points that are gross errors or outliers, in addition to other data points that are inliers and whose distribution can be explained by some set of model parameters. As such, it is able to smooth data sets in which outliers make up a significant portion of the data set. If a traditional technique for fitting a model to experimental data, such as least squares, were used instead of a robust fitting algorithm, these outlier data points could lead to inaccurate calculations of corneal properties, such as curvature.

The outliers can be due to extreme noise, erroneous measurements, or incorrect hypotheses about the interpretation of data, for example. In the case of corneal imaging specifically, the outliers can also be due to causes such as specular reflection, scarring or pathologies, curvature change after refractive surgery, blinking during data acquisition, interferences from eyelashes or eyelids, or other artifacts. By using RANSAC, these outliers can be detected during corneal power computation with no additional computation cost. As such, RANSAC makes corneal power measurements possible for patients for whom such measurements would otherwise be impossible for reasons such as excessive blinking Even for patients without excessive blinking, the embedded outlier detection allows patients to blink during the acquisition process to avoid a tear film breakup and to rest their eyes. Another advantage of detecting outliers as part of the corneal power computation is that it allows the acquisition of multiple successive scans which increase the total scan time. Multiple successive scans can be used for motion correction and corneal surface reconstruction, increasing SNR, and improving the accuracy of corneal power measurement.

Figure 7A:
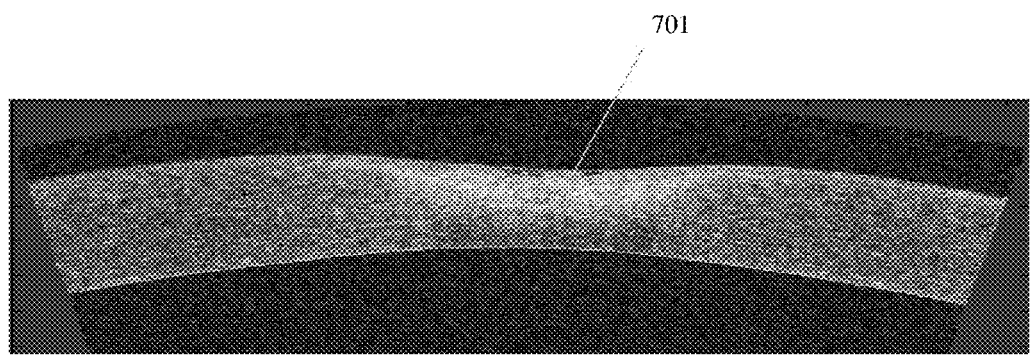
FIG. 7A shows Random Sample Consensus (RANSAC) fits to the anterior and posterior layers in a meridional B-scan of a cornea having pathology.
Figure 7B:
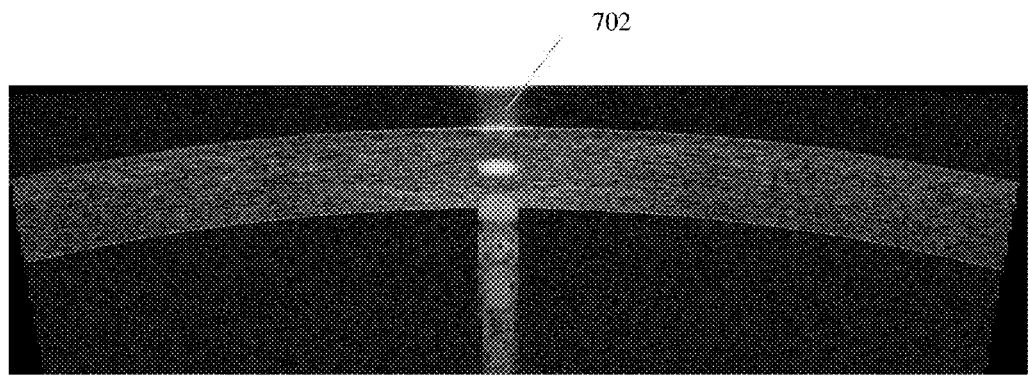
FIG. 7B shows RANSAC fits to the anterior and posterior layers in a meridional B-scan of a cornea with specular reflection.
Figure 8A:
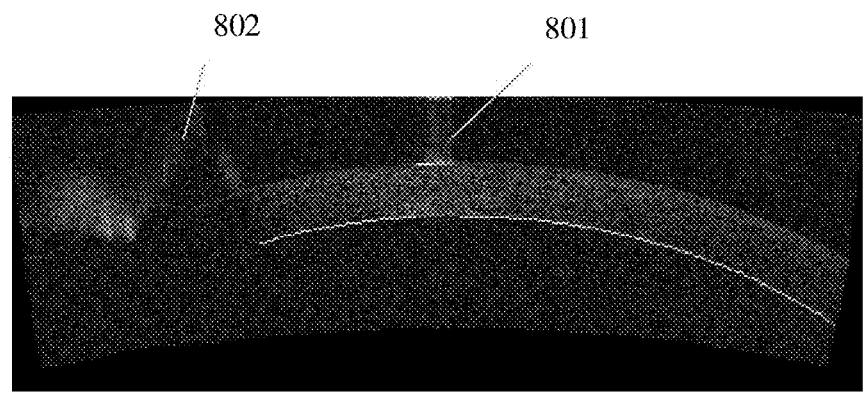
FIG. 8A illustrates how RANSAC makes fitting the anterior surface possible when the meridian scan contains specular reflection and artifacts caused by eyelid interference with the anterior surface.
Figure 8B:
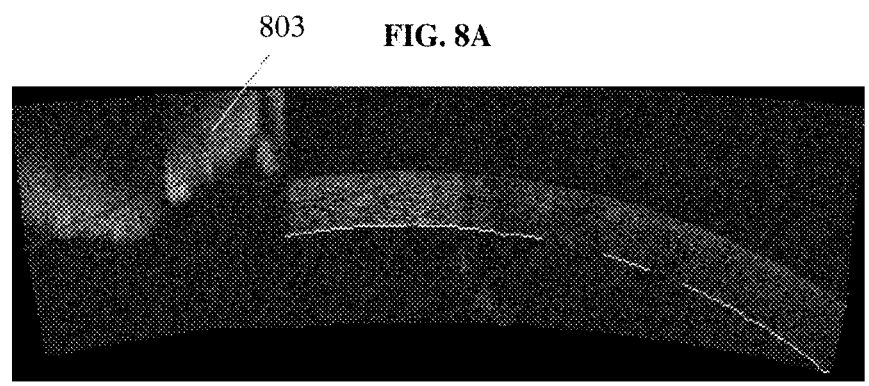
FIG. 8B illustrates how RANSAC makes fitting possible the anterior surface possible when the meridian scan contains artifacts caused by eyelid interference with the anterior surface.
Figure 8C:
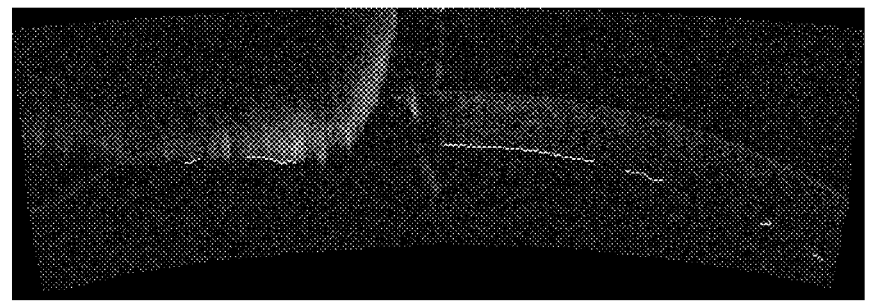
FIG. 8C illustrates a meridian scan that RANSAC could exclude from corneal power calculation using aspects of the present invention.
Figure 8D:
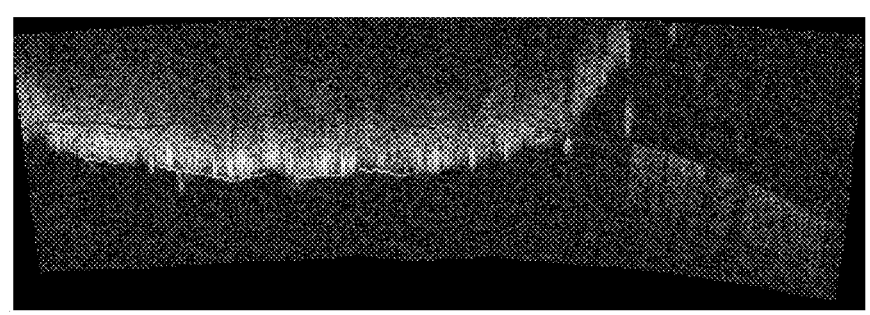
FIG. 8D illustrates a meridian scan that contains artifacts caused by a blink that could be excluded from corneal power calculation by determining the number of available anterior and posterior data points (inliers).

FIGS. 7A and 7B show RANSAC fits to the anterior and posterior layers in meridional B-scans of corneas having pathology 701 and specular reflection 702, respectively. Similarly, FIGS. 8A-D illustrate the occurrences of various artifacts, such as specular reflection, eye lid/lash interferences, and blink in OCT images and partial failure of the segmentation. FIG. 8A illustrates how RANSAC makes fitting the anterior surface possible when the meridian scan contains specular reflection 801 and artifacts 802 caused by eyelid interference with the anterior surface. FIG. 8B illustrates how RANSAC makes fitting the anterior surface possible when the meridian scan contains artifacts 803 caused by eyelid interference with the anterior surface. FIG. 8C illustrates a meridian scan that RANSAC could exclude from corneal power calculation by determining the number of posterior data points (inliers) and making a determination based on the number of inliers. FIG. 8D illustrates a meridian scan containing artifacts caused by a blink that could be rejected based on RANSAC analysis determining the number of available anterior and posterior data points (inliers) and making a determination based on the number of inliers. RANSAC makes fitting possible by identifying the data points falling into the model (e.g. quadratic, conic section, quadric, sphere, etc.) when there are interferences with data acquisition RANSAC also identifies the outliers in the data that can be excluded from corneal power computation and makes the corneal power computation possible when patients have excessive blinking The robust fitting algorithm may be used to determine the parameters of an appropriate fit, such as a $2^{nd}$ order polynomial. In such a case, RANSAC would be used to determine the coefficients for the equation $$y = a_1 x^2 + a_2 x + a_3$$

for the anterior surface, and $$y = p_1 x^2 + p_2 x + p_3$$

for the posterior surface. However, another fit may also be used, such as general equation of a conic section ($ax^2 + bxy + cy^2 + dx + ey + f = 0$).

Once a fit for each meridian is determined, the anterior and posterior radii of curvature can be calculated. For each meridian i, the anterior radius of curvature at the anterior vertex can be calculated by $$R_a^i = \frac{1}{|y''|}$$

where $$y' = 2a_1 x_0 + a_2$$
$$y'' = 2a_1$$

and $$x_0 = -\frac{a_2}{2a_1}$$

is the anterior vertex position. The posterior radius of curvature can be calculated by $$R_p^i = \frac{(1 + y'^2)^{\frac{3}{2}}}{|y''|}$$

where $$y' = 2p_1 x_0 + p_2$$
$$y'' = 2p_1.$$

From the radii of curvature, the anterior, posterior, and net corneal power for each meridian i can be calculated. The anterior power for meridian i is given by $$K_a^i = \frac{(n_1 - n_0)}{R_a^i}$$

the posterior power for meridian i is given by $$K_p^i = \frac{(n_2 - n_1)}{R_p^i}$$

and the net corneal power for meridian i is given by $$K^i = K_a^i + K_p^i - D \times K_a^i \times K_p^i / n_1$$

where

D=central corneal thickness $n_0$=1 Refractive index of air $n_1$=1.386 Refractive index of cornea $n_2$=1.333 Refractive index of aqueous humor.

The overall anterior, posterior, and net powers can then be calculated by averaging over N selected meridians:

$$K_a = \frac{\sum_{i=1}^{N} K_a^i}{N} \quad K_p = \frac{\sum_{i=1}^{N} K_p^i}{N} \quad K = \frac{\sum_{i=1}^{N} K^i}{N}.$$

Tracking and Registration

The sparse set of scans acquired through this method can also be used for alignment, repeat scans, and tracking the apex or vertex of the central cornea. By using the set of sparse B-scans that can be acquired quickly, the approximate model of corneal surface can be estimated in real time.

First, the anterior or posterior layer of each B-scan is segmented. One way in which the segmentation can be carried out is through the method using a dynamic programming framework, as described above. Then, if there is any specular reflection, it is removed. After any specular reflection is removed, any B-scan axial shift introduced during the acquisition process is corrected. For each B-scan, a $2^{nd}$ order polynomial ($y=a_1 x^2 + a_2 x + a_3$) is fitted to the central region of each anterior layer using RANSAC robust fit. The layer values (of an anterior layer) are then subtracted from $y(x=0)=a_3$.

A surface can then be fitted to the anterior or posterior layers of all of the meridional B-scans to model the corneal surface. Prior to fitting, the data can be centered. Centering the data (subtracting the mean $\bar{z}$ from from each value) reduces the degree of multi-collinearity. Multi-collinearity refers to a situation in which two or more independent variables in a regression model are highly linearly related. In general, the corneal surface can be modeled with a quadric surface. The quadric surface $z=f(x, y)$ models the corneal data in a general form and includes different shapes such as ellipsoid, paraboloid, and hyperboloid. The quadric surface is given by the general equation:

$$a_{11}x^2 + a_{22}y^2 + a_{33}z^2 + a_{12}xy + a_{13}xz + a_{23}yz + a_1 x + a_2 y + a_3 z + a_0 = 0.$$

Figure 9:
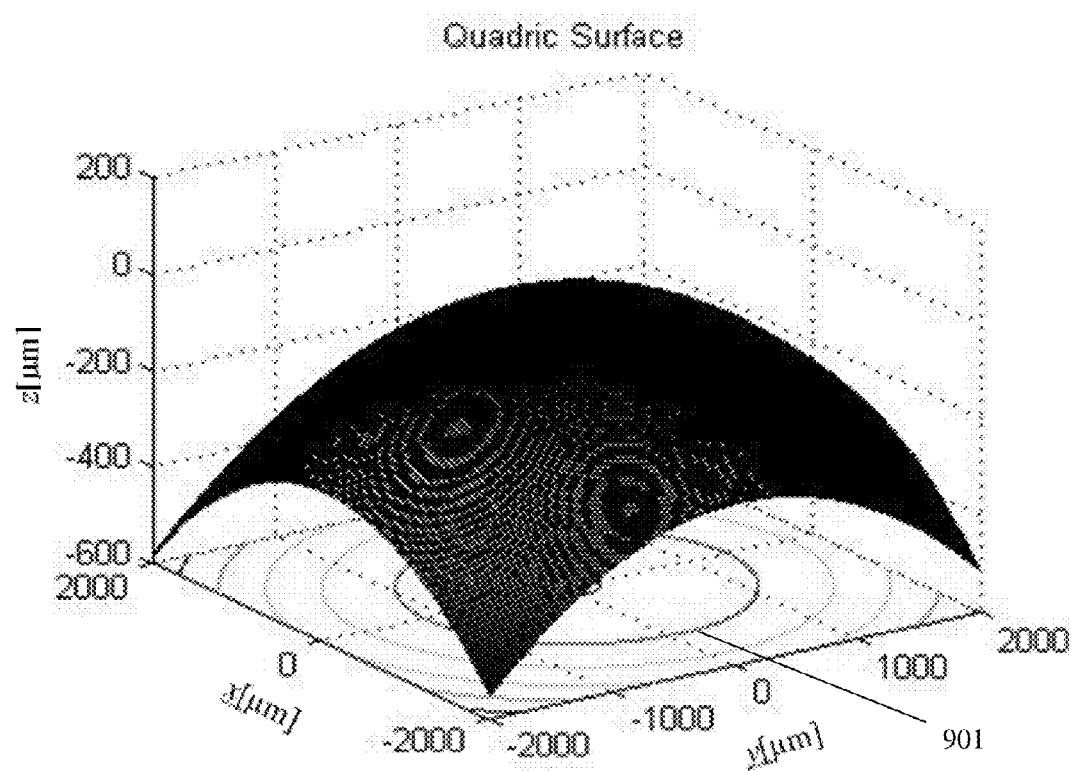
FIG. 9 is an example of a corneal surface model created using RANSAC.

As in the fitting algorithms described above, the coefficients ($a_{11}, a_{22}, a_{33}, a_{12}, a_{13}, a_{23}, a_1, a_2, a_3, a_0$) can be found by fitting the corneal data using a robust fitting algorithm, such as RANSAC. An example of a corneal surface model created using RANSAC is shown in FIG. 9. Note that the vertex position can be calculated at highest value in quadric surface. The corneal power is calculated based on the 3 mm diameter area 901 centered at the vertex position.

The model can then be used to determine rotation about three axes and the corneal apex. The equation for the quadric surface above can be rewritten as:

$$C(X^T A X + X^T L' + a_0') = 0$$

where $$A' = 1 \Big/ C \begin{bmatrix} a_{11} & a_{12}/2 & a_{13}/2 \\ a_{12}/2 & a_{22} & a_{23}/2 \\ a_{13}/2 & a_{23}/2 & a_{33} \end{bmatrix} = R \Lambda' R^T$$

$$L' = 1 \Big/ C \begin{pmatrix} a_1 \\ a_2 \\ a_3 \end{pmatrix} = -2 X_0^T \Lambda' R^T$$

$$a_0' = X_0^T \Lambda' X_0 R - 1$$

$X_0 = (x_0, y_0, z_0)^T$ The origin of the quadric surface $X = (x, y, z)^T$ A given point $R = R_x(\alpha) R_y(\beta) R_z(\gamma)$ Rotation matrix and $$R_x(\alpha) = \begin{bmatrix} 1 & 0 & 0 \\ 0 & \cos\alpha & \sin\alpha \\ 0 & -\sin\alpha & \cos\alpha \end{bmatrix}$$

$$R_y(\beta) = \begin{bmatrix} \cos\beta & 0 & -\sin\beta \\ 0 & 1 & 0 \\ \sin\beta & 0 & \cos\beta \end{bmatrix}$$

$$R_z(\gamma) = \begin{bmatrix} \cos\gamma & \sin\gamma & 0 \\ -\sin\gamma & \cos\gamma & 0 \\ 0 & 0 & 1 \end{bmatrix}.$$

The rotation angles of the corneal surface can then be calculated from the eigenvectors of A' as follows:

$$U = R^T = \begin{bmatrix} u_{11} & u_{12} & u_{13} \\ u_{21} & u_{22} & u_{23} \\ u_{31} & u_{32} & u_{33} \end{bmatrix}$$

$\alpha = a\tan(-u_{23}/u_{33})$ $\beta = a\sin(u_{13})$ $\gamma = a\tan(-u_{12}/u_{11})$.

The coordinates of the corneal apex are calculated by undoing the rotations of the quadric surface as follows:

$Y = XR$ $Y = (x', y', z')^T$ $z' = f'(x', y')$ $$\frac{\partial f'(x'_{apex}, y'_{apex})}{\partial x'} = 0$$

$$\frac{\partial f'(x'_{apex}, y'_{apex})}{\partial y'} = 0$$

$z'_{apex} = f'(x'_{apex}, y'_{apex})$ $Y_{apex} = (x'_{apex}, y'_{apex}, z'_{apex})^T$ $X_{apex} = Y_{apex} R^{-1}$ $X_{apex} = (x_{apex}, y_{apex}, z_{apex})^T$ Once the rotation angles of the corneal surface and the coordinates of the corneal apex are calculated, the information can be stored, used for alignment of the OCT system, used for data registration, or used to predict future eye positions. Tracking could be used during anterior segment acquisition by following the corneal surface movements, which enables a fast and efficient alignment and acquisition. Tracking can reduce the motion artifacts, reduce the acquisition time, and improve the repeatability of measurements such as thickness and power. This method can be also be expanded by using a Kalman Filter to track the corneal surface. By doing so, the processing can be made more efficient by predicting future corneal apex position and rotation angles. Prediction of future corneal apex position and rotation angles enables pre-emptive correction of positional or angular misalignment of the OCT system. The method can also be carried out using dense sets of data instead of sparse sets. Use of the method with dense scans may be more appropriate for registration, when calculations do not need to be determined in real time.

Tracking may also be carried out through other approaches. Transverse motion may be corrected for by integrating an x-y tracking mechanism in the sample arm of the OCT, which can provide real-time tracking of lateral displacement of the cornea. The tracking mechanism can be based on a number of different methods. For instance, it may be based on speckle tracking of light reflected from the cornea, the sclera, reflection tracking, or other similar techniques. As the displacement values are measured, they can be stored in a separate array for use in correction of B-scans and 2-D corneal surfaces. Z-motion may also be tracked and corrected. One way to correct for motion in the z direction with higher accuracy is to use scan patterns with repeated scans. For example, two consecutive B-scans that are obtained from the same location can be compared to ascertain the axial motion by calculating the displacement of tissue using cross-correlation-based techniques.

The effects of motion can also be reduced by using OCT systems that minimize the motion that occurs during acquisition of the sample. For example, ultrafast OCT systems can be used, reducing the acquisition time and therefore reducing the effects of motion. Similarly, linefield OCT or parallel OCT can be used. These allow all points along a B-scan to be obtained simultaneously, and as such, there is no motion within B-scans. Using these approaches to implement simultaneous correction of both lateral and z-motion can lead to improved calculations of corneal properties, such as corneal power.

Calibration of OCT System

The accuracy of the methods described here can also be enhanced through calibration of the OCT system. The OCT imaging system will need to be calibrated to obtain measurements with high accuracy such as field of view (FOV) in x and y, curvature of equal optical path length plane and the divergence or convergence of incident beam arriving at the sample or cornea. Such corrections may depend upon the optical design and scanning mechanism. Commercial OCT systems (such as Visante, Carl Zeiss Meditec, Inc. Dublin, Calif.) typically go through several calibration steps to improve accuracy and repeatability of measurements across different systems. FOV calibrations for applications such as corneal power need to have high accuracy because any errors in the lateral FOV will contribute to the errors in calculation of curvature of the cornea. Corrections for curvature of equal optical path length and divergence or convergence of the incident beam could be corrected by using ray tracing techniques and design parameters of the optical configuration. Additional experimental calibrations can be done by imaging flat samples or samples with known surface curvature profile. The following references are hereby incorporated by reference:

Patent Documents

U.S. Pat. No. 7,878,651 to O'Hara et al. "Refractive prescription using optical coherence tomography."

U.S. Pat. No. 7,365,856 to Everett et al. "Method of motion correction in optical coherence tomography imaging."

U.S. Pat. No. 7,452,077 to Meyer et al. "Image adjustment derived from optical imaging measurement data."

U.S. Pat. No. 7,481,536 to Wong et al. "Methods and systems for differentiating left and right eye images."

Non-Patent Literature

M. A. Choma et al. (2003). "Sensitivity advantage of swept source and Fourier domain optical coherence tomography." Optics Express 11(18): 2183-89.

J. F. de Boer et al. (2003) "Improved signal-to-noise ratio in spectral-domain compared with time-domain optical coherence tomography." Optics Letters 28(21): 2067-2069.

J. R. D'Errico (2006). *Understanding Gridfit*.

A. K. Gupta (2012). *Clinical Ophthalmology: Contemporary Perspectives*.

K. J. Hoffer (1993). The Hoffer Q formula: a comparison of theoretic and regression formulas. J. Cataract Refract. Surg. 19(6): 700-12.

D. Huang (2012). "Corneal power and IOL power calculation with OCT," presentation to Taiwan Academy of Ophthalmology, available at http://www.coollab.net/fileadmin/coollab_upload/coollab/docs/1Huang-OCT-based_IOL_formula-taiwan.pdf.

R. A. Leitgeb et al. (2003). "Performance of fourier domain vs. time domain optical coherence tomography." Optics Express 11(8): 889-94.

R. Leitgeb et al. (2004). "Ultrahigh resolution Fourier domain optical coherence tomography." Optics Express 12(10): 2156-65.

Y. Li et al. (2006). "Corneal pachymetry mapping with high-speed optical coherence tomography." Ophthalmology 111(5): 792-99.

Y. Li et al. (2008). "Keratoconus diagnosis with optical coherence tomography pachymetry mapping." Ophthalmology 115(12): 2159-66.

Y. Li et al. (2010). "Pachymetric mapping with Fourier-domain optical coherence tomography." J. Catarct. Refract. Surg. 36(5): 826-31.

M. Tang et al. (2006). "Measuring total corneal power before and after laser in situ keratomileusis with high-speed optical coherence tomography." J. Cataract Refract. Surg. 32(11): 1843-50.

M. Tang et al. (2010). "Corneal power measurement with Fourier-domain optical coherence tomography." J. Cataract Refract. Surg. 36(12): 2115-22.

A. Telea (2004). "An image inpainting technique based on the fast marching method." Journal of Graphics Tools 9(1): 25-36.

S. Timp et al. (2004). "A new 2D segmentation method based on dynamic programming applied to computer aided detection in mammography." Medical Physics 31(5): 958-971.

We claim:

1. A method for measuring the cornea of the eye with an optical coherence tomography system (OCT), said method comprising:

collecting a first set of OCT data over a series of transverse locations on the cornea of the eye within a time short enough to avoid any significant motion of the cornea;

processing the data collected in the first data set to generate a model of the cornea;

collecting a second set of OCT data over a series of transverse locations on the cornea of the eye;

determining one or both of the axial and transverse motion in the second data set by fitting the data in the second set to the model of the cornea created from the first set;

creating a motion-corrected data set from the second data set using one or both of the determinations of axial and transverse motion; and storing or displaying of the motion-corrected data set or information derived from the motion-corrected data set.

2. A method as described in claim 1, wherein the first data set consists of OCT data collected in a series of sparse scans.

3. A method as described in claim 2, wherein the first data set consists of OCT data collected in a series of meridional scans.

4. A method as described in claim 1, wherein the first data set consists of OCT data collected in a spiral scan.

5. A method as recited in claim 1, wherein the second data set consists of a series of dense scans.

6. A method as recited in claim 5, wherein the second data set consists of a series of meridional scans.

7. A method as recited in claim 6, further comprising determining which meridional scans had appreciable motion and not using them in further analysis.

8. A method as recited in claim 1, further comprising calculating a parameter that characterizes a property of the cornea using the motion-corrected data set.

9. A method as recited in claim 8, wherein the property is the curvature of the cornea.

10. A method as recited in claim 1, wherein the first and second data sets are collected using one of linefield or parallel OCT.

11. A method as recited in claim 1, wherein an ultrafast OCT system is used to collect the first and second data sets.

12. A method as recited in claim 1, wherein the motion corrected data set is used to create a model of the anterior and/or posterior surfaces of the cornea.

13. A method as recited in claim 1, wherein repeat scans are used to implement z-motion correction.

14. A method as recited in claim 1, wherein the model of the cornea is generated with a robust regression method.

15. A method as recited in claim 14, wherein the model of the cornea is generated with a Random Sample Consensus (RANSAC) fit.

16. A method as recited in claim 1, wherein the model of the cornea is used for alignment of the cornea.

17. A method as recited in claim 1, wherein the model of the cornea is used for repeat scans of the cornea.

18. A method as recited in claim 1, wherein the model of the cornea is used for tracking the apex or vertex of the cornea.

19. A method as recited in claim 1, further comprising collecting X-Y displacement tracking data from a tracking mechanism in the OCT system and processing the tracking data in addition to the OCT data to determine motion of the cornea.

20. A method as recited in claim 19, wherein the tracking mechanism is based on one of speckle tracking of light reflected from the cornea or sclera, reflection tracking, or pupil tracking.

21. A method as recited in claim 19, wherein the X-Y displacement values are acquired in parallel with the OCT scan, stored in a separate array, and used for lateral motion correction of B-scans and 2-D corneal surface maps.

22. A method as recited in claim 1, wherein the motion corrected data is used to generate a pachymetry map.

23. A method as recited in claim 1, wherein the motion corrected data is used to determine corneal power.

24. A method for determining the curvature of a cornea of an eye with an optical coherence tomography system (OCT), said method comprising:

collecting a first set of OCT data over a series of transverse locations on the cornea within a time short enough to avoid any significant motion of the cornea;

processing the first set of OCT data to generate a model of the cornea;

collecting a second set of OCT data over a series of transverse locations on the cornea;

determining axial and transverse motion in the second set of OCT data by fitting the data in the second set of OCT data to the model of the cornea created from the first set of OCT data;

creating a surface map of the cornea from the second set of OCT data based on the determined axial and transverse motion;

determining the axial curvature of the cornea from points on the surface map; and storing or displaying the axial curvature of the cornea.

25. The method of claim 24, wherein an axial curvature map is created based the determined axial curvature of the cornea from points on the surface map.

26. The method as recited in claim 25, further comprising generating k-values and axes of simulated keratometry from the axial curvature map.

27. The method as recited in claim 26, wherein the simulated keratometry k-values and axes are computed from the axial curvature by sampling the axial curvature map at a given zone diameter with the same elevation.

28. The method as recited in claim 26, further comprising using the simulated keratometry for planning refractive surgery.

* * * * *